United States Patent [19]

Chen et al.

[11] Patent Number: 5,215,900
[45] Date of Patent: Jun. 1, 1993

[54] MICROBIAL TRANSFORMATION OF A SUBSTITUTED PYRIDINONE USING STREPTOMYCES SP. MA6804

[75] Inventors: Shieh-Shung T. Chen, Morganville; George Doss, Westfield, both of N.J.

[73] Assignee: Merck & Co., Inc., Rahway, N.J.

[21] Appl. No.: 712,216

[22] Filed: Jun. 7, 1991

[51] Int. Cl.$^5$ .............................................. C12P 17/14
[52] U.S. Cl. .................................. 435/120; 435/253.5; 435/121
[58] Field of Search ...................... 435/120, 121, 253.5

[56] References Cited

U.S. PATENT DOCUMENTS

| | | | |
|---|---|---|---|
| 3,715,358 | 2/1973 | Witzel et al. | 514/345 |
| 3,835,143 | 9/1974 | Witzel et al. | 546/297 |
| 3,846,553 | 11/1974 | Shen et al. | 514/345 |

*Primary Examiner*—Douglas W. Robinson
*Assistant Examiner*—Marian C. Knode
*Attorney, Agent, or Firm*—Charles M. Caruso; Roy D. Meredith; Carol S. Quagliato

[57] ABSTRACT

Fermentation of the microorganism Streptomyces sp. (MA6804), ATTC No. 55095, in the presence of the HIV reverse transcriptase inhibitor

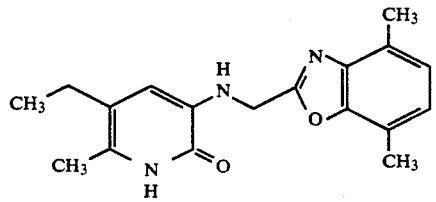

yields a 5-(1-hydroxy)ethyl analog which is useful in the prevention or treatment of infection by HIV and the treatment of AIDS.

3 Claims, No Drawings

MICROBIAL TRANSFORMATION OF A SUBSTITUTED PYRIDINONE USING STREPTOMYCES SP. MA6804

This application is related to copending U.S. application Ser. No. 539,643 filed on Jun. 18, 1990; Ser. No. 539,681 filed on Jun. 18, 1990; Ser. No. 539,760 filed on Jun. 18, 1990; Ser. No. 599,968 filed on Oct. 18, 1990; and Ser. No. 608,104 filed on Nov. 1, 1990 all now abandoned.

The present invention relates to a novel process for the preparation of compound (I)

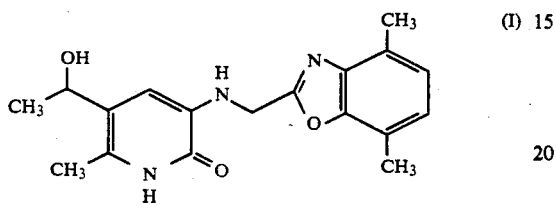

comprising fermentation of compound (II), an inhibitor of the reverse transcriptase encoded by human immunodeficiency virus (HIV),

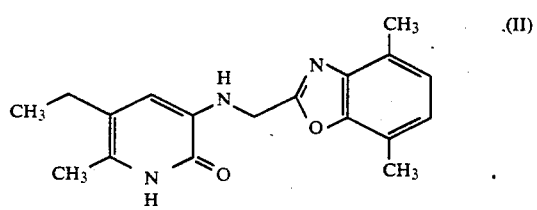

with the microorganism Streptomyces sp. (MA6804), ATTCC No. 55095. Compound (I) and the pharmaceutically acceptable salts thereof inhibit the reverse transcriptase encoded by HIV and are of value in the prevention of infection by HIV, the treatment of infection by HIV and the treatment of the resulting acquired immune deficiency syndrome (AIDS).

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is reverse transcription of the RNA genome by a virally encoded reverse transcriptase to generate DNA copies of HIV sequences, a required step in viral replication. It is known that some compounds are reverse transcriptase inhibitors and are effective agents in the treatment of AIDS and similar diseases, e.g., azidothymidine or AZT.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, an endonuclease and an HIV protease [Toh, H. et al., EMBO J. 4, 1267 (1985); Power, M.D. et al., Science, 231, 1567 (1986); Pearl, L. H. et al., Nature 329, 351 (1987)].

The compound prepared by the novel process of this invention is an inhibitor of HIV reverse transcriptase. Furthermore, the compound of the present invention does not require bio-activation to be effective.

SUMMARY OF THE INVENTION

The HIV reverse transcriptase inhibitor, compound (I), is produced by the novel process of this invenition involving the fermentation of the microorganism Streptomyces sp. (MA6804), ATCC No. 55095, in the presence of substrate compound (II). Compound (I) is the 5-(1-hydroxy)ethyl analog of compound (II). The biotransformation is accomplished under submerged aerobic conditions in an aqueous carbohydrate medium containing a nitrogen nutrient at a pH of about 7 for a sufficient time to produce compound (I).

DETAILED DESCRIPTION OF THE INVENTION AND PREFFERED EMBODIMENTS

The novel process of this invention comprises fermentation of the microorganism Streptomyces sp. (MA6804) in the presence of substrate compound (II)

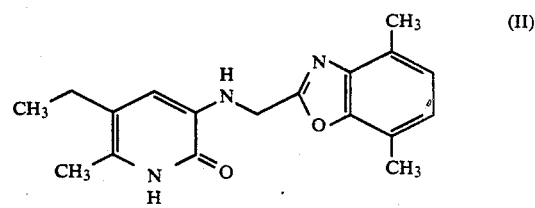

in a nutrient medium, and isolation of the resulting biotransformation product, compound (I), in a conventional manner.

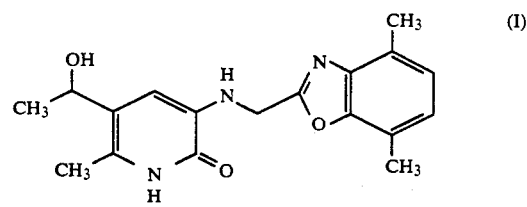

A biologically pure sample of Streptomyces sp. (MA6804) is deposited in the permanent culture collection of the American Type Culture Collection, 12301 Parklawn Drive in Rockville, Md., with Accession Number ATCC 55095.

General growth characteristics

Good growth on yeast malt extract, glycerol asparagine, inorganic salts-starch, oatmeal, and trypticase soy agars. Growth occurs at 27° and 37° C. Culture also grows well in liquid media such as yeast dextrose broth.

Colony morphology (on yeast malt extract agar)

Substrate mycelium is medium yellow (87 m.Y) and colonies are opaque, raised, lobate and rubbery. The colony surface is rough. Aerial mycelia appear after 2 days incubation and are white in color (263 White). Spore mass, when present is light gray (264 1. Gy) to light brown gray (63 1. br. Gy).

Micromorphology

Aerial mycelium (0.57 μm dia.) radiate from the substrate mycelium and is straight. In mature cultures, aerial mycelia terminate in chains of spores that are borne in loops and open spirals.

Miscellaneous physiological reactions

Culture produces melanoid pigments in tryptone yeast extract broth, yeast extract broth, and peptone yeast extract iron agar in 2–3 days. Starch is not hydrolyzed.

On the basis of the taxonomic analysis performed thus far, the microorganism Streptomyces sp. (MA6804) has tentatively been identified as a strain of *Streptomyces lavendulae* pending verification by further testing.

The following is a general description of Streptomyces sp. strain MA6804. Observations of growth, general cultural characteristics and carbon source utilization were made in accordance with the methods of Shirling and Gottleib (*Internat. J. System. Bacteriol.* 16: 313–340). Chemical composition of the cells was determined using the methods of Lechevalier (in *Actinomycete Taxonomy*, A. Dietz and D. W. Thayer, Ed. Society for Industrial Microbiology, 1980). Coloration of the culture was determined by comparison with color standards contained in the Inter-Society Color Council-Bational Bureau of Standards Centroid Color Charts (U.S. Dept. of Commerce National Bureau of Standards supplement to NBS Circular 553, 1985).

Source

The culture was isolated from a soil sample taken from the Como house garden, Melbourne, Australia.

Analysis of Cell Wall Composition

Peptidoglycan contains L-diaminopimelic acid: whole cell sugar analysis reveals galactose, mannose, madurose, and traces of glucose.

Yeast Extract—Malt Extract

Growth: Good
Aerial Mycelium: Light gray (264 l.Gray) to light brown gray (63 l. gy. br); sporophores borne in loops and open spirals
Soluble Pigment: None noted
Substrate Mycelium: Medium yellow (87 m.Y)

Glucose—Asparagine

Growth: Good
Aerial Mycelium: Pink gray (10 pk Gray); sporophores borne in loops and open spirals
Soluble Pigment: None noted
Substrate Mycelium: Medium gray yellow (90 gy. Y)

Inorganic Salts—Starch

Growth: Good
Aerial Mycelium: Light gray (264 l. Gray); sporophores borne in loops and open spirals
Soluble Pigment: None noted
Substrate Mycelium: Pale yellow (89 p. Y)

Oatmeal Agar

Growth: Good
Aerial Mycelium: Light gray (264 l.Gray); sporophores borne in loops and open spirals
Soluble Pigment: None noted
Substrate Mycelium: Yellow white (92 y. White)

| Carbohydrate Utilization Pattern of Streptomyces sp. MA6804 at 21 Days | |
| --- | --- |
| Carbon Source | Utilization* |
| D-arabinose | 0 |
| L-arabinose | 0 |
| cellobiose | 2 |
| D-fructose | 1 |
| inositol | 0 |
| α-D-lactose | 0 |
| β-D-lactose | 0 |
| D-maltose | 2 |
| D-mannitol | 0 |
| D-mannose | 2 |
| D-raffinose | 0 |
| L-rhamnose | 0 |
| sucrose | 0 |
| D-xylose | 0 |
| L-xylose | 0 |
| α-D-glucose (control) | 2 |

*3 = good utilization
2 = moderate utilization
1 = poor utilization
0 = no utilization

Sigma Water

Growth: Fair
Aerial Mycelium: Transparent; sporophores borne in loops and open spirals
Soluble Pigment: None noted

Czpak

Growth: Fair
Aerial Mycelium: Transparent; sporophores borne in loops and open spirals
Soluble Pigment: None noted

Peptone Iron

Growth: Good
Melanin: Positive

In general, compound (I), the 5-(1-hydroxy)ethyl oxidation product, can be produced by culturing (fermenting) the above-described microorganism in the presence of an appropriate concentration of substrate compound (II) in an aqueous nutrient medium containing sources of assimilable carbon and nitrogen, preferably under submerged aerobic conditions (e.g. shaking culture, submerged culture, etc.). An appropriate concentration of the parent compound in the aqueous medium ranges from 0.01 mg/ml 0.5 mg/ml, preferably 0.05 mg/ml; less than 0.01 mg/ml is inefficient and greater than 0.5 mg/ml can inhibit the culture. The aqueous medium is incubated at a temperature between 26° C. and 29° C., preferably 27° C.; culture growth will be inhibited below this temperature range and culture death will occur above this temperature range. The aqueous medium is incubated for a period of time necessary to complete the oxidative biotransformation as monitored by HPLC, usually for a period of about 48 hours, on a rotary shaker operating at about 220 rpm with a throw of about 2 in. The aqueous medium is maintained at a pH between 6 and 8, preferably about 7, at the initiation and termination (harvest) of the fermentation process. A higher or lower pH will cause the culture to die. The desired pH may be maintained by the use of a buffer such as morpholinoethanesulfonic acid (MES), morpholinopropanesulfonic acid (MOPS), and the like, or by choice of nutrient materials which inherently possess buffering properties, such as production media described herein below.

The preferred sources of carbon in the nutrient medium are certain carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids, and the like.

The carbon and nitrogen sources, though advantageously employed in combination, need not be used in their pure form because less pure materials which contain traces of growth factors and considerable quantities of mineral nutrients are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

Substrate compound (II) can be obtained by synthetic organic procedures, as described elsewhere in this application.

Submerged aerobic cultural conditions are preferred for the production of compound (I) in massive amounts. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of compound (I).

Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is substantially the same as or different from the medium utilized for the production of compound (I) and is generally autoclaved to sterilize the medium prior to inoculation. The fermentation medium is generally adjusted to a pH between 6 and 8, preferably about 7, prior to the autoclaving step by suitable addition of an acid or base, preferably in the form of a buffering solution. Temperature of the seed medium is maintained between 26° C. and 29° C., preferably 27° C.; culture growth will be inhibited below this range and culture death will occur above this range. Incubation of the seed medium is usually conducted for a period of about 10 to 30 hours, preferably 18 hours, on a rotary shaker operating at 220 rpm; the length of incubation time may be varied according to fermentation conditions and scales. Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

Preferred culturing/production media for carrying out the fermentation include the following media:

|  | g/l |
|---|---|
| Seed Medium A | |
| Dextrose | 1.0 |
| Dextrin | 10.0 |
| Beef Extract | 3.0 |
| Ardamine pH | 5.0 |
| NZ Amine Type E | 5.0 |
| $MgSO_4.7H_2O$ | 0.05 |
| $K_2HPO_4$ | 0.3 |
| Adjust pH to 7.1 | |
| Add $CaCO_3$ | 0.5 g/l |
| Transformation Medium B | |
| Glucose | 10 |
| Hycase SF | 2 |
| Beef Extract | 1 |
| Corn Steep Liquor | 3 |
| Adjust pH to 7.0 | |
| Transformation Medium C | |
| Mannitol | 5 |
| Glycerol | 5 |
| Hycase SF | 2 |
| Beef extract | 1 |
| Corn Steep Liquor | 3 |
| Adjust pH to 7.0 | |

The biotransformation product, compound (I), can be recovered from the culture medium by conventional means which are commonly used for the recovery of other known biologically active substances. Compound (I) is found in the cultured mycelium and filtrate, which are obtained by filtering or centrifuging the cultured broth, and accordingly can be isolated and purified from the mycelium and the filtrate by a conventional method such as concentration under reduced pressure, lyophilization, extraction with a conventional solvent, such as methylene chloride and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred recovery method is solvent extraction, particularly using methylene chloride. A preferred purification method involves the use of chromatography, especially HPLC, using a silica gel column and an eluant mixture composed of water and an organic solvent such as methanol, acetonitrile and the like. A preferred eluant is composed of water and acetonitrile and is run through the column in a linear gradient.

Compound (I) is useful in the inhibition of HIV reverse transcriptase, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, compound (I) of this invention is useful in treating infection by HIV after suspected past exposure to HIV by, e.g., blood transfusion, organ transplant, accidental needle stick, exchange of body fluids, bites or exposure to patient blood during surgery.

Reverse Transcriptase Assay

The assay measures the incorporation of tritiated deoxyguanosine monophosphate by recombinant HIV reverse transcriptase (HIV $RT_R$) (or other RT) into acid-precipitable cDNA at the Km values of dGTP and poly r(C).oligo d(G)$_{12-18}$. Compound (I) of the present invention inhibits this incorporation.

Thirty uL of a reaction mixture containing equal volumes of: 500 mM Tris.HCl (pH 8.2), 300 mM $MgCl_2$, 1200 mM KCl, 10 mM DTT, 400 µg/mL poly r(c).oligo d(G) [prepared by dissolving 1.5 mg (25 U) poly r(C).oligo d(G) in 1.5 ml sterile distilled $H_2O$ and diluting to 400 µg/ml], 0.1 µuCi/µl [$^3$H] dGTP, 160 µM dGTP, was added to 10 µl sterile distilled $H_2O$, 2.5 µl of potential inhibitor. Ten µL of 3.2 nM purified HIV $RT_R$ in tubes. The mixture was incubated at 37° C. for 45 minutes.

After incubation was complete, the tubes were cooled in ice for 5 minutes. Ice-cold 13% TCA containing 10 mM $NaPP_i$ (200 µl) was added and the mixture incubated on ice for 30 minutes. The precipitated cDNA was removed by filtration using presoaked glass filters [TCA, $NaPP_i$]. The precipitate was then washed with 1N HCl, 10 mM $NaPP_i$. The filter discs were then counted in a scintillation counter.

Under these conditions [dGTP] and poly r(C).oligo d(G)$_{12-18}$ each are approximately equal to the appropriate Km value. Approximately 5–6,000 cpm of [$^3$H] GMP are incorporated into acid-precipitable material. The RT reaction is concentration-and time-dependent. DMSO (up to 5%) does not affect enzyme activity.

Compound (I) was evaluated using the methodology described above. The calculated $IC_{50}$ of compound (I) was found to be about 430 nM, thereby demonstrating and confirming the utility of compound (I) as an effective HIV reverse transcriptase inhibitor.

The following examples are given for the purpose of illustrating the present invention and should not be construed as being limitations on the scope or spirit of the instant invention.

EXAMPLE 1

Preparation of Substrate Compound (II):
3-[((4,7-Dimethylbenzoxazol-2-yl)-methyl)amino]-5-ethyl-6-methyl-2(1H)-pyridinone Step A: Preparation of 3-amino-5-ethyl-6-methyl-2-(1H)-pyridinone Step 1: Preparation of 5-ethyl-6-methyl-3-nitro-2(1H)-pyridinone A mixture of 2-ethyl-3-oxobutanal, sodium salt (7.5 g, 55 mmol), nitroacetamide (6.6 g, 63 mmol), aqueous piperidinium acetate (4.4 mL) [prepared from glacial acetic acid (42 mL), water (100 mL) and piperidine (72 mL)] in water (45 mL) was stirred at room temperature for 22 hours. The yellow precipitate was collected by filtration and air dried to yield 5-ethyl-6-methyl-3-nitro-2(1H)-pyridinone.

Step 2: Preparation of 3-amino-5-ethyl-6-methyl-2(1H)-pyridinone

A yellow solution of the 5-ethyl-6-methyl-3-nitro-2(1H)-pyridinone (10 g, 55 mmol) in a mixture of methanol and tetrahydrofuran (100 mL, 1:1 v/v) was reduced catalytically in the presence of 7% palladium on charcoal (0.7 g) under and atmosphere of hydrogen (50 psi) at room temperature over a period of 3.5 hours. The resultant mixture was filtered through a small pad of Celite. The filtrate was concentrated under reduced pressure (15 torr) to provide the corresponding aminopyridone.

Step B: Preparation of 2-chloromethyl-4,7-dimethylbenzoxazole

To a solution of 2,5-dimethyl-6-aminophenol (0.67 g, 4.9 mmol) in methylene chloride, solid ethyl 2-chloroiminoacetate hydrochloride (0.85 g, 4.9 mmol) was added. The resultant slurry was stirred at room temperature for 18 hours, then filtered through a plug of diatomaceous earth and concentrated under reduced pressure (15 torr). The solid residue was subjected to column chromatography on silica gel (50 g, eluted with 1% methanol in chloroform). Collection and concentration of appropriate fractions yielded the title benzoxazole.

Step C: Preparation of 3-[(4,7-dimethylbenzoxazol2-yl)methylamino]-5-ethyl-6-methyl-2(1H)pyridinone A mixture of 3-amino-5-ethyl-6-methyl-2-(1H)-pyridinone (0.23 g, 1.5 mmol), 2-chloromethyl-4,7-dimethylbenzoxazole (0.29 g, 1.5 mmol), diisopropylethylamine (0.39 g, 3 mmol) in acetonitrile (50 mL) was refluxed under an atomosphere of nitrogen for 12 hours. The resultant mixture was concentrated under reduced pressure (15 torr). The residue was then subjected to column chromatography on silica gel (100 g, elution with 4% methanol in chloroform). Collection and concentration of appropriate fractions provided the title compound.

Anal. Calcd for $C_{18}H_{21}N_3O_2$: C, 69.43; H, 6.80; N, 13.49. Found C, 69.32; H, 6.66; N, 13.47.

EXAMPLE 2

Microorganism and Culture Conditions

A frozen vial (2.0 ml) of culture (MA6804) ATCC No. 55095 was used to inoculate a 250 ml baffled shake flask containing 50 ml of an autoclaved (sterilized) seed medium consisting of (in units of grams/liter) dextrin 10.0, dextrose 1.0, beef extract 3.0, ardamine pH (Yeast Products, Inc.) 5.0, N-Z Amine type E 5.0, $MgSO_4$.7-$H_2O$ 0.05, $K_2HPO_4$ 0.3, and $CaCO_3$ 0.5. The pH of the seed medium was adjusted to 7.1 before autoclaving. The seed was incubated in the seed medium at 27° C. for 18 hours on a rotary shaker operating at 220 rpm. A 1 ml aliquot of the resulting seed medium was used to inoculate a 50 ml non-baffled shake flask containing 10 ml of the following previously autoclaved (sterilized) transformation medium B.[1] A DMSO solution of substrate compound (II) was added to the fermentation at zero hour to achieve a final concentration of 0.05 mg/ml. The shake flask contents were subsequently incubated for 2 days at 27° C. on a rotary shaker operating at 220 rpm. This procedure was followed twenty times and the twenty resultant broths were combined for isolation and purification.

1. Transformation medium B consisted of (in grams/liter) glucose 10.0; Hycase SF 2.0; beef extract 1.0; corn steep liquor 3.0; where the pH was adjusted to 7.0 before autoclaving.

Isolation and Purification Procedure for the Broth

The whole broth (200 ml) of transformation media B was extracted with methylene chloride (2×200 ml). Methylene chloride extracts were combined, dried over sodium sulfate, and concentrated under vacuum to an oily residue. The residue was dissolved in methanol and subjected to high performance liquid chromatography (HPLC) purification.

HPLC was carried out on Whatman Partisil 10 ODS-3, 9.4 mm×25 cm column at room temperature and monitored at 250 nm. The column was developed at 3 ml/min with linear gradient from H₂O—CH₃CN, 75:25, to H₂O—CH₃CN, 55:45 in 35 minutes. The compounds were collected during repeated injections of the above described extract. The fractions at retention time 18.6 and 21.4 minutes were pooled respectively, and evaporated to remove solvents to yield 0.5 mg of a compound characterized as a degradation product of substrate compound (II), and 0.5 mg. of compound (I) characterized as the 5-(1-hydroxy)ethyl oxidation product, respectively.

EXAMPLE 3

Characterization

The structure of biotransformation product (I) was determined by proton NMR run in CDCl₃. Compound (I) was shown to result from hydroxylation at —CH₂— of the ethyl side chain.

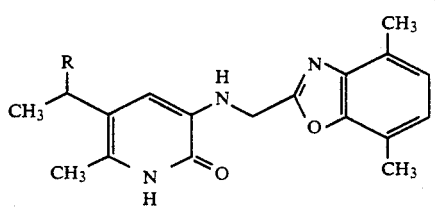

| Compound | R |
|---|---|
| (I) | —OH |
| (II) | —H |

Hydroxylation of C-1 of the ethyl side chain in compound (I) was evident from the appearance of the terminal methyl group as a doublet at 1.40 ppm (rather than a triplet at 1.15 ppm in parent compound (II)), and the appearance of a CHOH quartet near 4.9 ppm instead of the methylene quartet at ~2.4 ppm in the parent compound.

EXAMPLE 4

Synthetic Preparation of Compound (I):
3-[(4,7-Dimethylbenzoxazol-2-yl)-methylamino]-5-(1-hydroxyethyl)-6-methyl-2(1H)-pyridinone The title compound is obtained by employing substantially the same procedures as described in Example 1, with the following modifications.

1) The 2-ethyl-3-oxobutanal, sodium salt, used as a starting material in Step A, Step 1, is replaced by

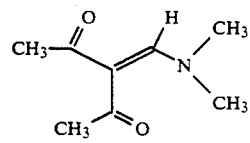

to obtain the intermediate 3-nitro-5-acetyl-6-methyl-2(1H)-pyridinone.

2) The 3-nitro-5-acetyl-6-methyl-2(1H) -pyridinone intermediate is next treated with sodium borohydride (approx. 1 molar equivalent) in ethanol at room temperature for a sufficient time to reduce the 5-acetyl group to a 5-(1-hydroxyethyl) group. The reaction mixture is then treated with a small amount of acid, and the product is recovered and purified using standard methods.

3) The remaining steps of Example 1, from Step A, Step 2, to the end, are substantially followed except that the 5-ethyl-6-methyl-3-nitro-2-(1H)-pyridinone and its intermediates used therein are replaced by 3-nitro-5-(1-hydroxyethyl)-6-methyl-2(1H)-pyridinone and its intermediates.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed:

1. A process for the preparation of a compound of formula (I)

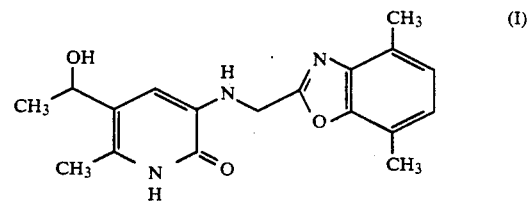

comprising the steps of culturing a microorganism Streptomyces sp. MA6804 ATCC 55095 in a nutrient medium containing assimilable sources of nitrogen and carbon and substrate compound (II)

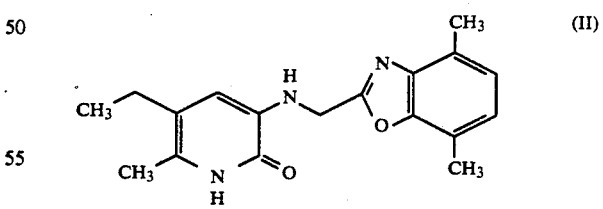

under aerobic conditions until a substantial amount of the compound of formula (I) is produced and isolating the compound produced.

2. The process of claim 1 wherein the temperature is 26°–29° C.

3. The process of claim 2 wherein the temperature is 27° C.